United States Patent
Murakami et al.

(10) Patent No.: US 8,841,614 B1
(45) Date of Patent: Sep. 23, 2014

(54) SAMPLE STRUCTURE ANALYZING METHOD, TRANSMISSION ELECTRON MICROSCOPE, AND COMPUTER-READABLE NON-TRANSITORY RECORDING MEDIUM

(71) Applicant: Kabushiki Kaisha Toshiba, Tokyo (JP)

(72) Inventors: Takeshi Murakami, Yokohama (JP); Haruko Akutsu, Yokosuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/106,352

(22) Filed: Dec. 13, 2013

(30) Foreign Application Priority Data

Jun. 11, 2013 (JP) .................................. 2013-122927

(51) Int. Cl.
- *H01J 37/26* (2006.01)
- *G01N 23/20* (2006.01)

(52) U.S. Cl.
CPC .......... *G01N 23/20058* (2013.01); *H01J 37/26* (2013.01)
USPC ............................. 250/307; 250/306; 250/311

(58) Field of Classification Search
USPC ......................................... 250/306, 307, 311
See application file for complete search history.

(56) References Cited

U.S. PATENT DOCUMENTS

| | | | | |
|---|---|---|---|---|
| 4,211,924 A | * | 7/1980 | Muller et al. ................. | 250/311 |
| 4,553,030 A | | 11/1985 | Tokiwai et al. | |
| 4,880,977 A | * | 11/1989 | Tomita et al. ................. | 250/311 |
| 5,350,921 A | * | 9/1994 | Aoyama et al. ............... | 250/311 |
| 5,466,934 A | * | 11/1995 | Adams et al. ................. | 250/307 |
| 5,576,543 A | * | 11/1996 | Dingley ........................ | 250/311 |
| 5,744,800 A | * | 4/1998 | Kakibayashi et al. ........ | 250/311 |
| 7,928,377 B2 | * | 4/2011 | Ishitani et al. ................ | 250/306 |
| 8,008,621 B2 | * | 8/2011 | Jeong et al. ................... | 250/307 |
| 8,253,099 B2 | * | 8/2012 | Nicolopoulos et al. ....... | 250/307 |
| 8,476,588 B2 | * | 7/2013 | He et al. ........................ | 250/307 |
| 2003/0234359 A1 | * | 12/2003 | Drown et al. ................. | 250/307 |
| 2004/0188610 A1 | * | 9/2004 | Hirose .......................... | 250/310 |
| 2010/0019145 A1 | * | 1/2010 | Jeong et al. ................... | 250/307 |
| 2011/0284744 A1 | * | 11/2011 | Zewail et al. ................. | 250/307 |
| 2012/0025073 A1 | * | 2/2012 | Kumar .......................... | 250/307 |

FOREIGN PATENT DOCUMENTS

| | | |
|---|---|---|
| JP | 2007-064962 A | 3/2007 |
| JP | 2010-256261 A | 11/2010 |
| JP | 2011-021926 A | 2/2011 |

* cited by examiner

*Primary Examiner* — David A Vanore

(74) *Attorney, Agent, or Firm* — Holtz Holtz Goodman & Chick PC

(57) ABSTRACT

In accordance with an embodiment, a sample structure analyzing method includes generating a beam and then applying the beam to a plurality of observation regions on a sample, and acquiring a plurality of diffraction images from the beam which has passed through the sample; and comparing the acquired diffraction images, and judging the difference between the observation regions from the comparison result, or identifying the grain boundary of crystal constituting the sample.

16 Claims, 6 Drawing Sheets

SAMPLE STRUCTURE ANALYZING METHOD, TRANSMISSION ELECTRON MICROSCOPE, AND COMPUTER-READABLE NON-TRANSITORY RECORDING MEDIUM

CROSS REFERENCE TO RELATED APPLICATIONS

This application is based upon and claims the benefit of priority from the prior Japanese Patent Application No. 2013-122927, filed on Jun. 11, 2013, the entire contents of which are incorporated herein by reference.

FIELD

Embodiments described herein relate generally to a sample structure analyzing method, a transmission electron microscope, and a computer-readable non-transitory recording medium.

BACKGROUND

There has been known a technique for applying an electron beam to a thin film sample by using a transmission electron microscope, detecting the electron beam which has passed through the thin film sample to acquire a plurality of electron images, and comparing contrast between the obtained electron images to observe the sample structure.

However, for example, even if the electron images are acquired over a crystal grain boundary, a contrast difference cannot be well observed in some cases. In such cases the technique of judging by the contrast of the transmission electron image causes problems in the identification of the crystal grain boundary and the measurement of a shape.

DETAILED DESCRIPTION

In accordance with an embodiment, a sample structure analyzing method includes generating a beam and then applying the beam to a plurality of observation regions on a sample, and acquiring a plurality of diffraction images from the beam which has passed through the sample; and comparing the acquired diffraction images, and judging the difference between the observation regions from the comparison result, or identifying the grain boundary of crystal constituting the sample.

Embodiments will now be explained with reference to the accompanying drawings. Like components are provided with like reference signs throughout the drawings and repeated descriptions thereof are appropriately omitted.

The drawings are attached to illustrate the invention and assist in the understanding of the illustration. Therefore, the shapes, dimensions, and ratios in some parts may be different from those in an actual apparatus, but can be properly designed and modified by reference to the following explanations and known arts. Although an electron beam is described as an example of a beam in the present specification, the beam is not limited thereto and is also applicable to other charged particle beams such as an ion beam.

(1) Embodiment 1

Figure 1:
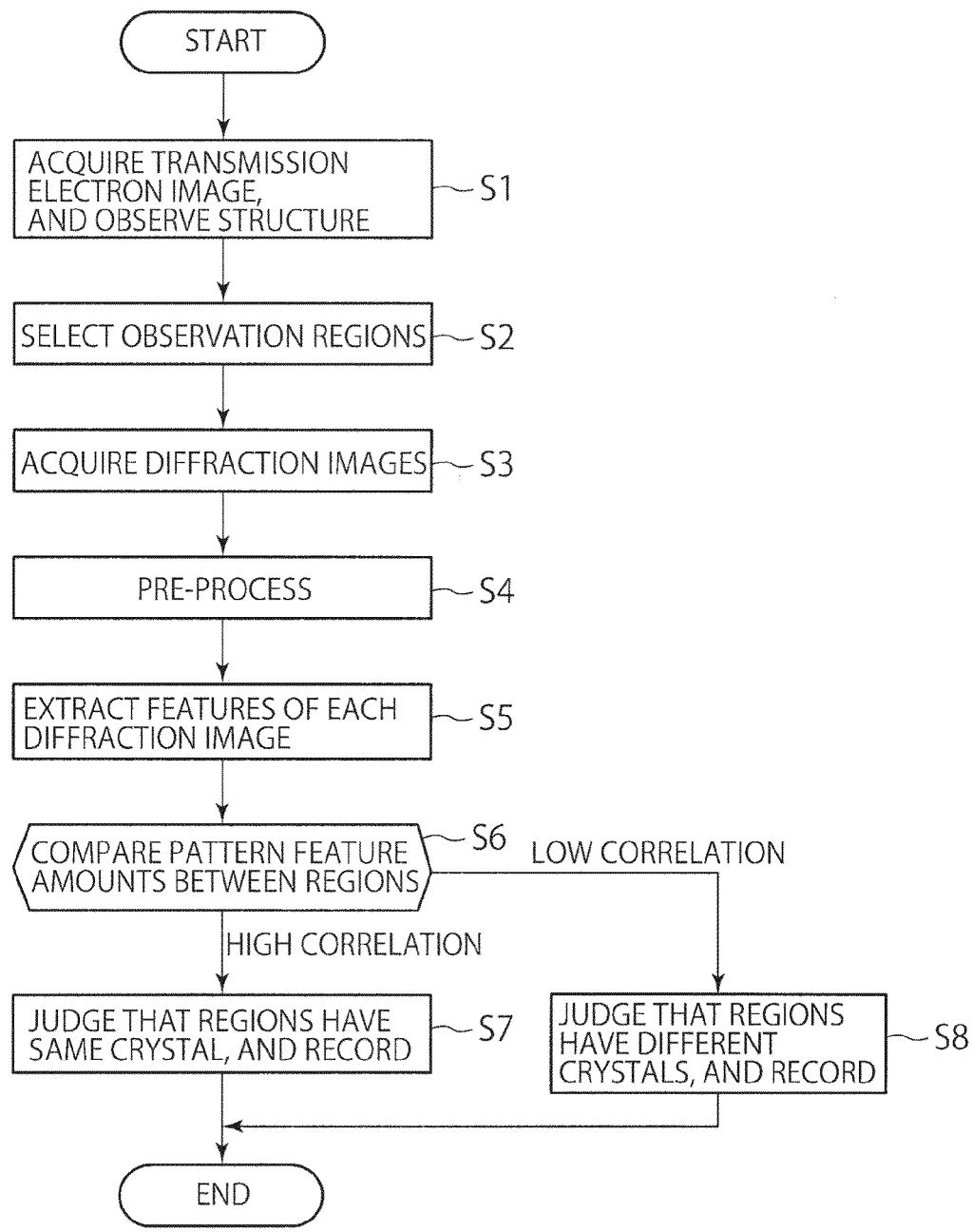
FIG. 1 is a flowchart showing the general procedure of a sample structure analyzing method according to Embodiment 1.

A schematic procedure of a sample structure analyzing method according to Embodiment 1 is described with reference to a flowchart in FIG. 1.

First, an electron beam is generated and then applied to a sample. A transmission electron image is acquired from the transmitted electron beam, and the general structure of the sample is observed (step S1).

A plurality of observation regions are selected as regions of interest from the observation result in step S1 (step S2).

The electron beam is then applied to each of the selected observation regions for each predetermined pitch, and a plurality of diffraction images are acquired (step S3).

The obtained diffraction images are pre-processed for the subsequent processing. More specifically, multivalued images are converted to two-value images by two-dimensional filtering such as noise elimination, smoothing, and sharpening (digitalization).

Feature amounts of each of the digitalized diffraction images are then extracted (step S5). The feature amounts are compared between the observation regions, and the degree of correlation between the diffraction images is judged (step S6).

When the correlation between the observation regions is high, these regions are judged to be regions having the same crystal, and the judgment result is recorded together with information on the regions (step S7).

On the other hand, when the correlation is low, the crystals are judged to be different in at least one of material and crystal orientation, and the judgment result is recorded together with information on the regions (step S8).

Figure 2:
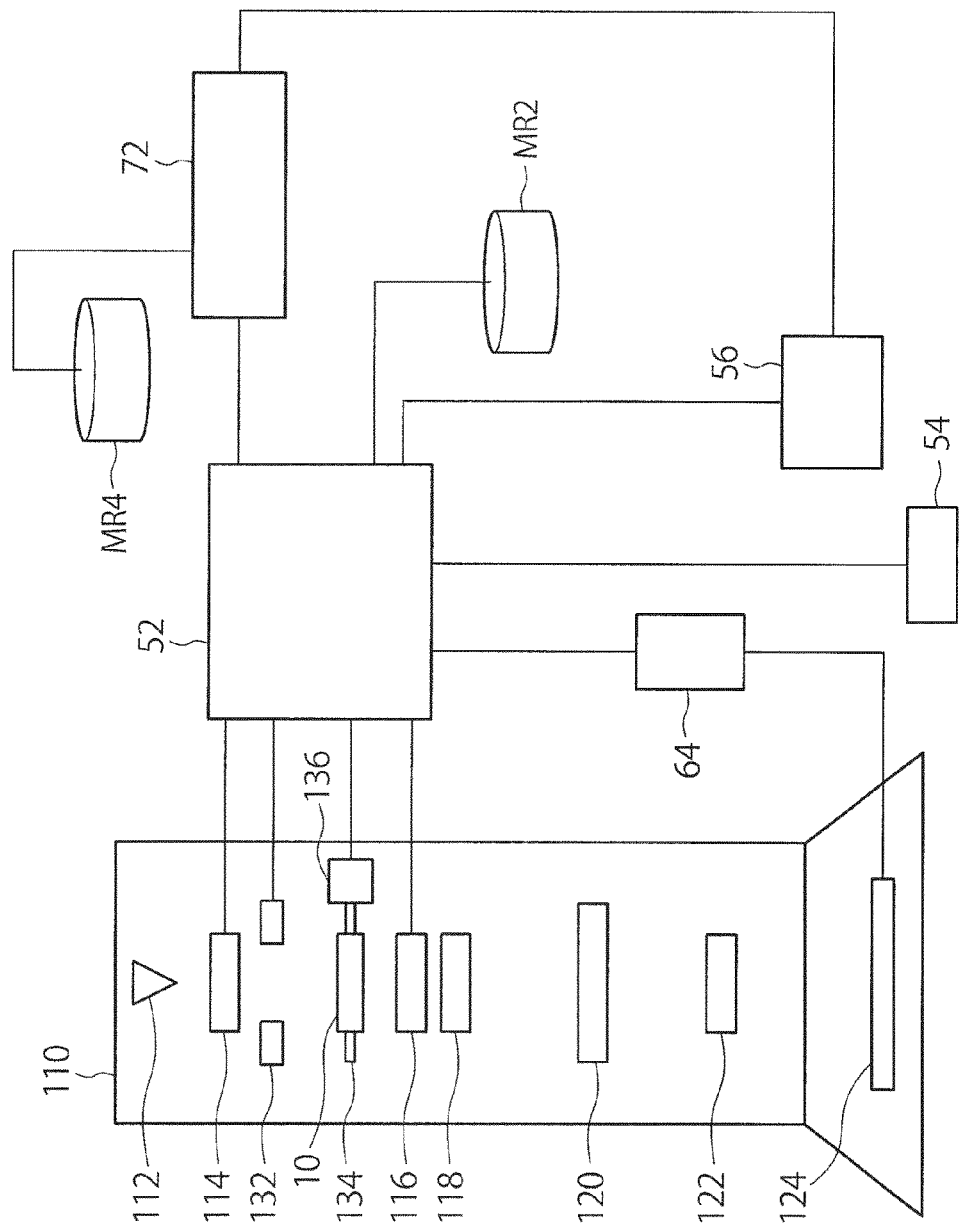
FIG. 2 is a block diagram showing the general configuration of a transmission electron microscope for conducting the sample structure analyzing method according to Embodiment 1.

FIG. 2 is a block diagram showing the general configuration of a transmission electron microscope for conducting the sample structure analyzing method according to Embodiment 1. The transmission electron microscope shown in FIG. 2 includes a main unit 110, a control unit 52, an input unit 54, a monitor 56, a signal processing unit 64, and an image analyzing unit 72.

The main unit 110 includes an electron gun 112, a condensing lens 114, a deflector 132, a sample holder 134, an actuator 136, an objective lens 116, a limiting field stop 118, an intermediate lens 120, a projection lens 122, and a fluorescent screen 124. These components are disposed in a column. The main unit 110 is coupled to an unshown high-vacuum pump, and is used after the column has been vacuumized.

A sample 10 is a thin film sample which is extracted from a device to be observed and which is produced by fabricating to such a thickness as to allow the transmission of electromagnetic radiations. The sample 10 is held on the sample holder 134 and located between the condensing lens 114 and the objective lens 116.

The sample holder 134 is coupled to the actuator 136. When the actuator 136 operates in accordance with a control signal sent from the control unit 52, the sample holder 134 moves the sample 10 in an X-Y two-dimensional plane, or inclines the sample 10 at a given angle of inclination. In the present embodiment, the actuator 136 corresponds to, for example, a sample moving unit.

The deflector 132 deflects the electron beam at a given deflection angle when a control signal is sent from the control unit 52, and the sample 10 is thereby scanned.

The input unit 54 is an interface for an operator to input, to the control unit 52, various parameters necessary for the observation of the sample 10, such as optical conditions of the main unit 110, information regarding the observation region selected to acquire the diffraction image, and threshold data to judge the degree of correlation between the diffraction images.

The image analyzing unit 72 extracts feature amounts from the diffraction images respectively acquired in the different observation regions, and then compares the feature amounts with a predetermined threshold input from the input unit 54. The image analyzing unit 72 thereby judges whether the observation regions are made of crystal of the same material and crystal of the same orientation, or identifies a crystal grain boundary from the difference of the feature amounts. A memory MR4 is connected to the image analyzing unit 72. Data on the judgment result and the identification result are stored in the memory MR4.

The image analyzing unit 72 is connected to the monitor 56. The above-mentioned judgment result and identification result can be displayed by the monitor 56.

In the present embodiment, the image analyzing unit 72 corresponds to, for example, an analyzing unit.

The electron beam emitted from the electron gun 112 is condensed by the condensing lens 114, and deflected by the deflector 132, and then passes through the sample 10 while scanning the sample 10. The electron beam which has passed through the sample 10 enters the fluorescent screen 124 via the objective lens 116, the limiting field stop 118, the intermediate lens 120, and the projection lens 122. An electron microscope image or a diffraction image of the sample 10 is formed on the fluorescent screen 124, and photoelectrically transformed so that a signal is sent to the signal processing unit 64.

The signal processing unit 64 is connected to the control unit 52. The signal processing unit 64 processes a signal sent from the fluorescent screen 124 to form an electron microscope image or a diffraction image, and sends the image to the control unit 52. The control unit 52 stores the electron microscope image or diffraction image of the sample 10 in a memory MR2, and also displays the image on the monitor 56 so that the operator can observe the image.

In the present embodiment, the electron gun 112 and the condensing lens 114 correspond to, for example, a beam applying unit. The deflector 132, the actuator 136, the objective lens 116, the limiting field stop 118, the intermediate lens 120, the projection lens 122, the fluorescent screen 124, the signal processing unit 64, and the control unit 52 correspond to, for example, a diffraction image acquiring unit.

A more specific processing procedure of the sample structure analyzing method according to Embodiment 1 using the transmission electron microscope shown in FIG. 2 is described with reference to FIG. 3 and FIG. 4.

First, for the observation of the general structure of the sample 10, a low-magnification transmission electron image is acquired and displayed on the monitor 56. The operator watches the transmission electron image displayed on the monitor 56, and selects a plurality of observation regions where a structural analysis should be conducted, and then inputs, from the input unit 54, data to specify the selected observation regions.

A magnification is then set in such a manner that the selected observation regions come into view, and a diffraction image of each of the observation regions of the sample 10 is acquired. More specifically, the control unit 52 supplies a control signal to the condensing lens 114 to adjust a beam flux, and also supplies a control signal to the deflector 132 to adjust an irradiation pitch. The actuator 136 moves the sample 10 in the X-Y two-dimensional plane, and the observation regions of the sample 10 are scanned with the electron beam in the meantime. The irradiation pitch is set in accordance with the size of crystal constituting the sample 10. For example, a pitch of several nm is set.

Figure 3:
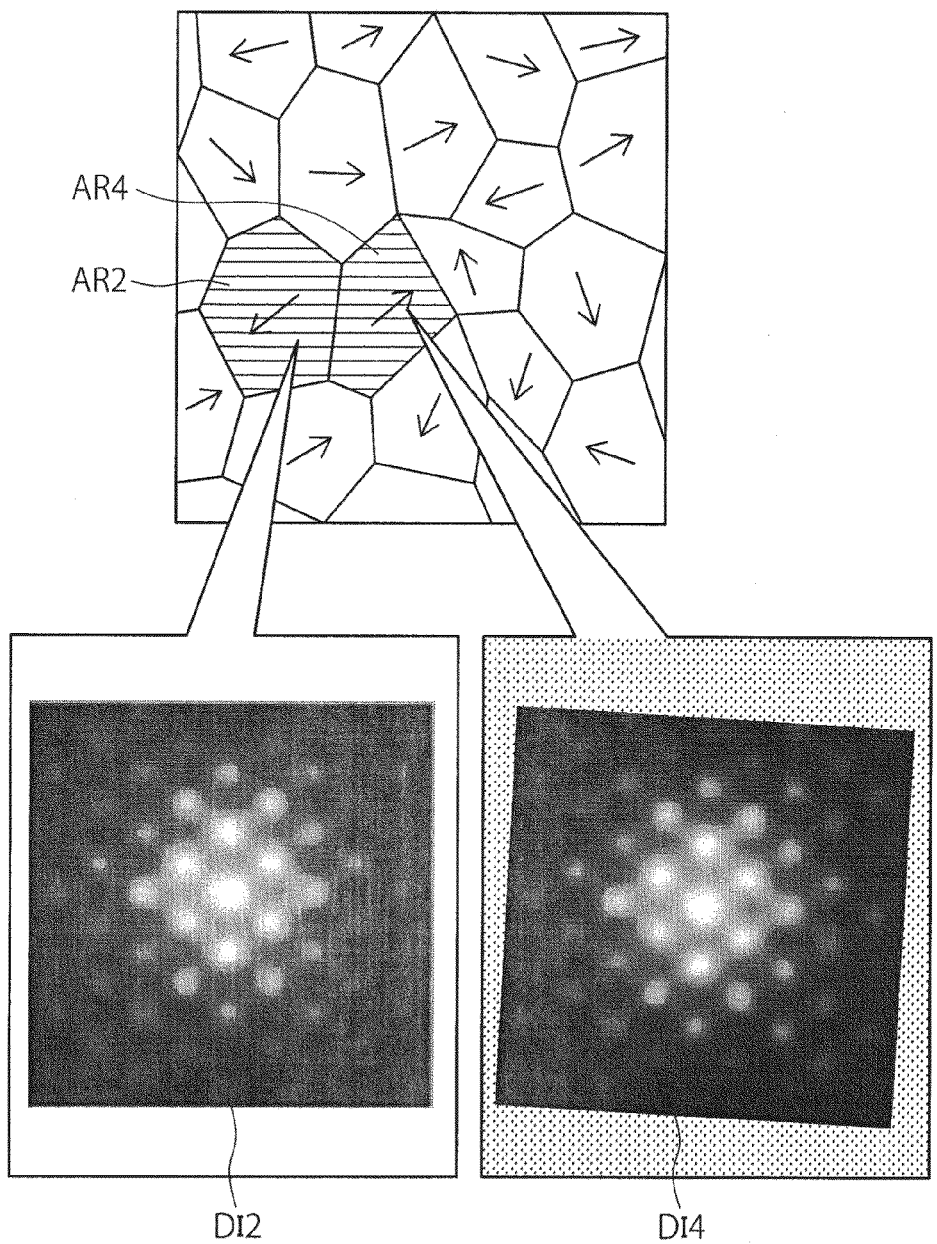
FIG. 3 is a diagram showing an example of diffraction images obtained from two regions different in crystal orientation.

FIG. 3 is a schematic diagram showing an example of selected observation regions, and shows an example of diffraction images acquired from the respective observation regions. Diffraction images DI2 and DI4 in FIG. 3 are obtained by scanning observation regions AR2 and AR4 with the electron beam, respectively.

In the schematic diagram of the observation regions shown in the upper part of FIG. 3, the observation regions AR2 and AR4 are made of the same material, but have opposite crystal orientations as indicated by arrows. Therefore, the diffraction images DI2 and DI4 in the lower part of FIG. 3 are slightly different in contrast.

To analyze the structure of the sample 10, features of the diffraction images DI2 and DI4 are extracted by the image analyzing unit 72. More specifically, a pattern edge of each diffraction image is extracted by, for example, Hough transform, and its geometrical features are extracted. Specific examples of the geometrical features include, for example, the distance between characteristic parts in the diffraction image, the area of each diffraction image, barycentric coordinates, and central coordinates.

The image analyzing unit 72 then performs pattern matching between the diffraction images DI2 and DI4, calculates a matching score (the degree of correspondence), and compares the obtained matching score with a predetermined threshold. If the matching score is more than the predetermined threshold, the degree of correlation between the observation regions AR2 and AR4 is high, and these observation regions are judged to be regions having the same crystal structure. The judgment result is displayed on the monitor 56 and stored in the memory MR4. On the other hand, if the matching score is equal to or less than the predetermined threshold, the degree of correlation between the observation regions AR2 and AR4 is low, and these observation regions are judged to be regions having different crystal structures. The judgment result is displayed on the monitor 56 and stored in the memory MR4.

The threshold is not limited to a single threshold. For example, it is possible to prepare and use a first threshold to judge whether crystal orientations are the same even if the material is the same, and a second threshold to judge whether materials are different.

Figure 4:
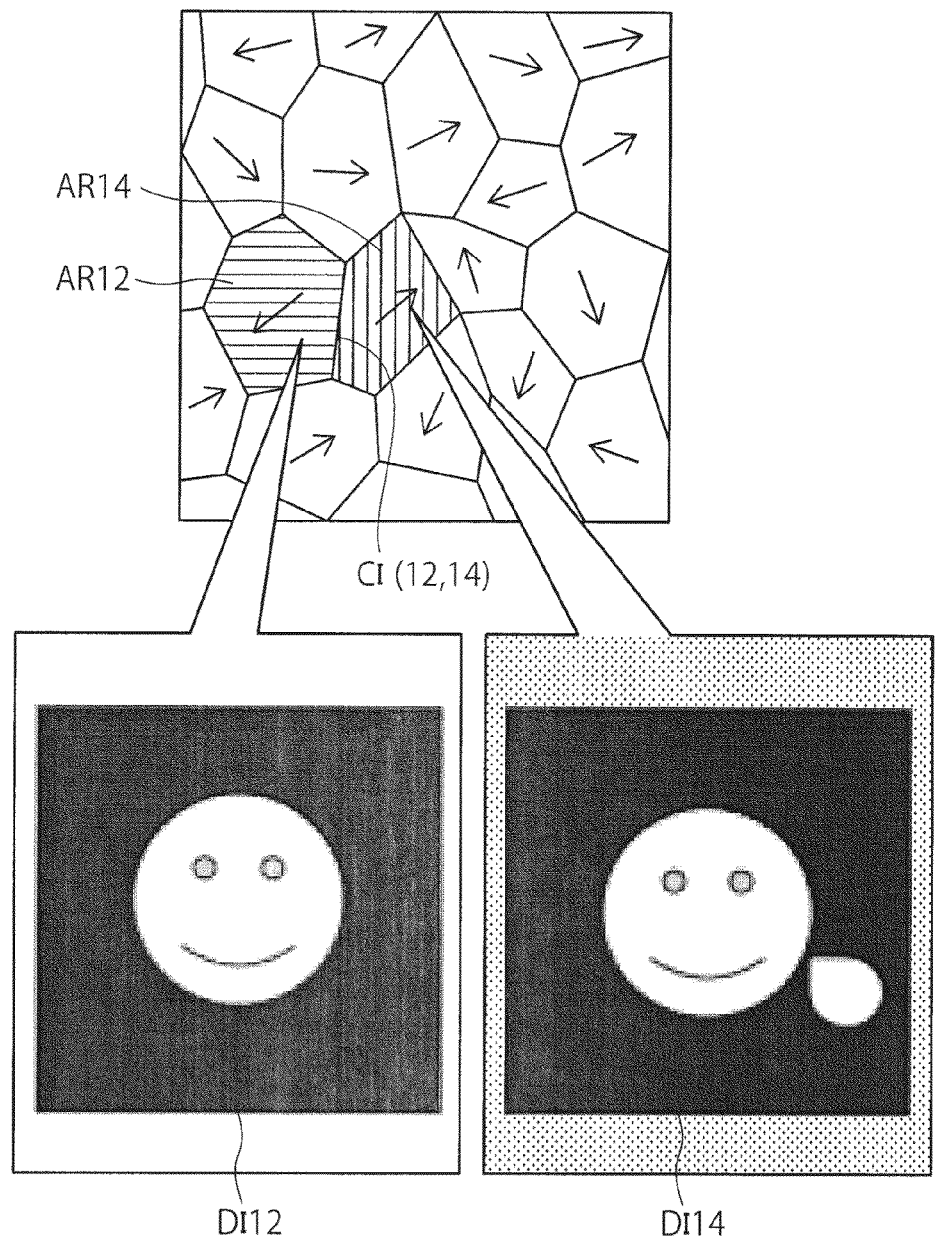
FIG. 4 is a schematic diagram illustrating diffraction images obtained from two regions different in material and crystal orientation.

FIG. 4 shows a schematic diagram of another example of selected observation regions, and a schematic diagram of diffraction images obtained from the respective observation regions. Diffraction images DI12 and DI14 represent images obtained by scanning observation regions AR12 and AR14 with the electron beam, respectively.

In the schematic diagram of the observation regions shown in the upper part of FIG. 4, the observation regions AR12 and AR14 have opposite crystal orientations as indicated by arrows, and are made of different materials. As a result, the diffraction images DI12 and DI14 obtained from these regions are apparently different as schematically shown in the lower part of FIG. 4. In the case shown in FIG. 4, the degree of correlation between the observation regions AR12 and AR14 can be detected by a threshold lower than the threshold used in FIG. 3.

Thus, the lower threshold is first used to classify the observation regions by whether their constituent materials are the same or different, and then the higher threshold is used. It is thereby possible to classify the observation regions made of the same material by whether their crystal orientations are the same or different.

The sample structure analyzing method according to the present embodiment compares a plurality of diffraction images acquired from the beam which has passed through the sample, and judges the difference between the observation regions from the comparison result. Consequently, it is possible to accurately distinguish parts that have little contrast in the transmission electron image only; for example, an interface of an amorphous layer, or an interface between heavy elements.

The transmission electron microscope according to the present embodiment includes analyzing unit for comparing a plurality of diffraction images acquired from the beam which has passed through the sample, and judging the difference between the observation regions from the comparison result. Consequently, it is possible to accurately distinguish parts that have little contrast in the transmission electron image only.

(2) Embodiment 2

Figure 5:
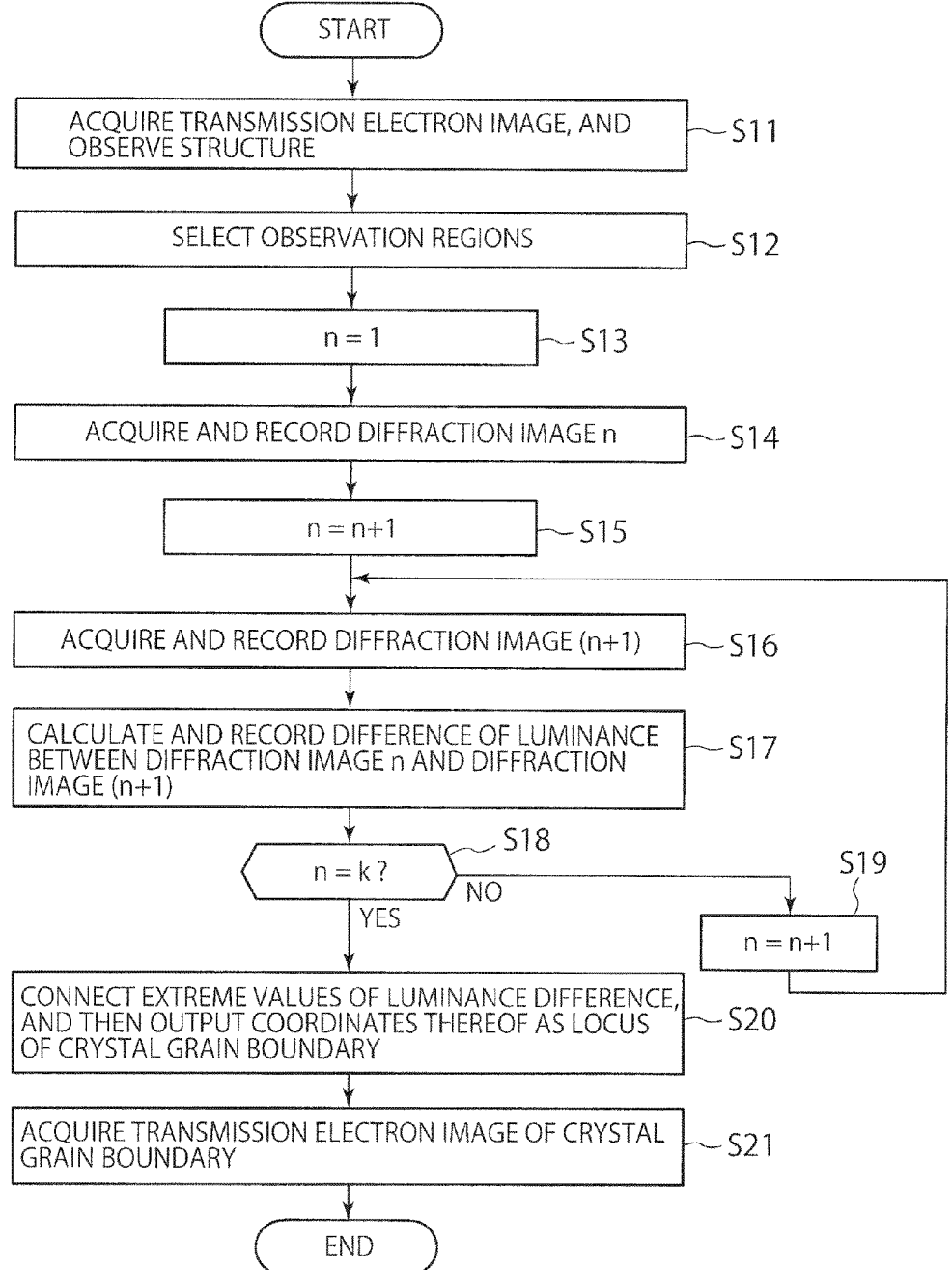
FIG. 5 is a flowchart showing the general procedure of a sample structure analyzing method according to Embodiment 2.

A schematic procedure of a sample structure analyzing method according to Embodiment 2 is described with reference to a flowchart in FIG. 5.

First, as in Embodiment 1, an electron beam is generated and then applied to a sample. A transmission electron image is acquired from the transmitted electron beam, and the general structure of the sample is observed (step S11).

A plurality of observation regions are then selected from the observation result in step S11 (step S12). In the present embodiment, there are k (k is a natural number equal to or more than 2) observation regions.

n (n is a natural number) is set to 1 (step S13), and then the electron beam is applied to the observation region 1 (n=1) in the form of a line or a dot pattern. A diffraction image n (n=1) is acquired and recorded (step S14). The obtained diffraction image n has positional information and luminance information for each pixel. Thus, if the luminance information is considered as a value on a Z-axis, the diffraction image can be represented by (X, Y, luminance) three-dimensional coordinates.

n is then increased to n=n+1 (step S15), and the electron beam is applied to an observation region 2 (n=2) adjacent to the observation region 1 in the form of a line or a dot pattern, and then a diffraction image 2 (n=2) is acquired and recorded (step S16).

When the diffraction images 1 and 2 are acquired, the difference of luminance between the diffraction images 1 and 2 is calculated and recorded (step S17).

As described above, the diffraction images are acquired from the respective neighboring observation regions, and then the difference of luminance therebetween is calculated and recorded. This procedure is repeated to the last observation region, that is, until n=k (steps S18 and S19, steps S16 and S17).

When the luminance differences between the diffraction images are calculated for all the observation regions (YES in step S18), the recorded luminance difference is differentiated by a luminance value to find extreme values. If the obtained extreme values are connected, a series of coordinates of the connected extreme values will be a locus of a crystal grain boundary (step S20).

Finally, the sample 10 is scanned while the electron beam is being deflected in such a manner that the locus of the crystal grain boundary will be the center of each scan line. A transmission electron image of the crystal grain boundary is thereby acquired (step S21).

A more specific processing procedure of the sample structure analyzing method according to Embodiment 2 is more specifically described. In the present embodiment as well, the transmission electron microscope shown in FIG. 2 can be used to analyze the sample structure.

First, as in Embodiment 1 described above, for the observation of the general structure of the sample 10, a low-magnification transmission electron image is acquired, and displayed on the monitor 56. The operator watches the transmission electron image displayed on the monitor 56, and selects a plurality of observation regions where a structural analysis should be conducted, and then inputs, from the input unit 54, data to specify the selected observation regions.

A magnification is then set by the control unit 52 in such a manner that the selected observation regions come into view. A control signal is sent to the main unit 110, and a diffraction image n (n=1 to k) of each of the observation regions of the sample 10 is obtained accordingly. Whenever the diffraction image is acquired, its image data is stored in the memory MR2.

The image data regarding the diffraction image n (n=1 to k) is sent to the image analyzing unit 72 via the control unit 52, and is transformed into three-dimensional coordinate data (X, Y, luminance). The difference of luminance between the diffraction images is then calculated, and stored in the memory MR4

When diffraction images n are then acquired for all the observation regions (n=k) and all the luminance differences between these diffraction images are calculated, extreme values of the luminance difference are found by the image analyzing unit 72. Then the coordinates of the pixels that provide the obtained extreme values are connected, displayed on the monitor 56 as a locus of a crystal grain boundary, and stored in the memory MR4.

Figure 6:
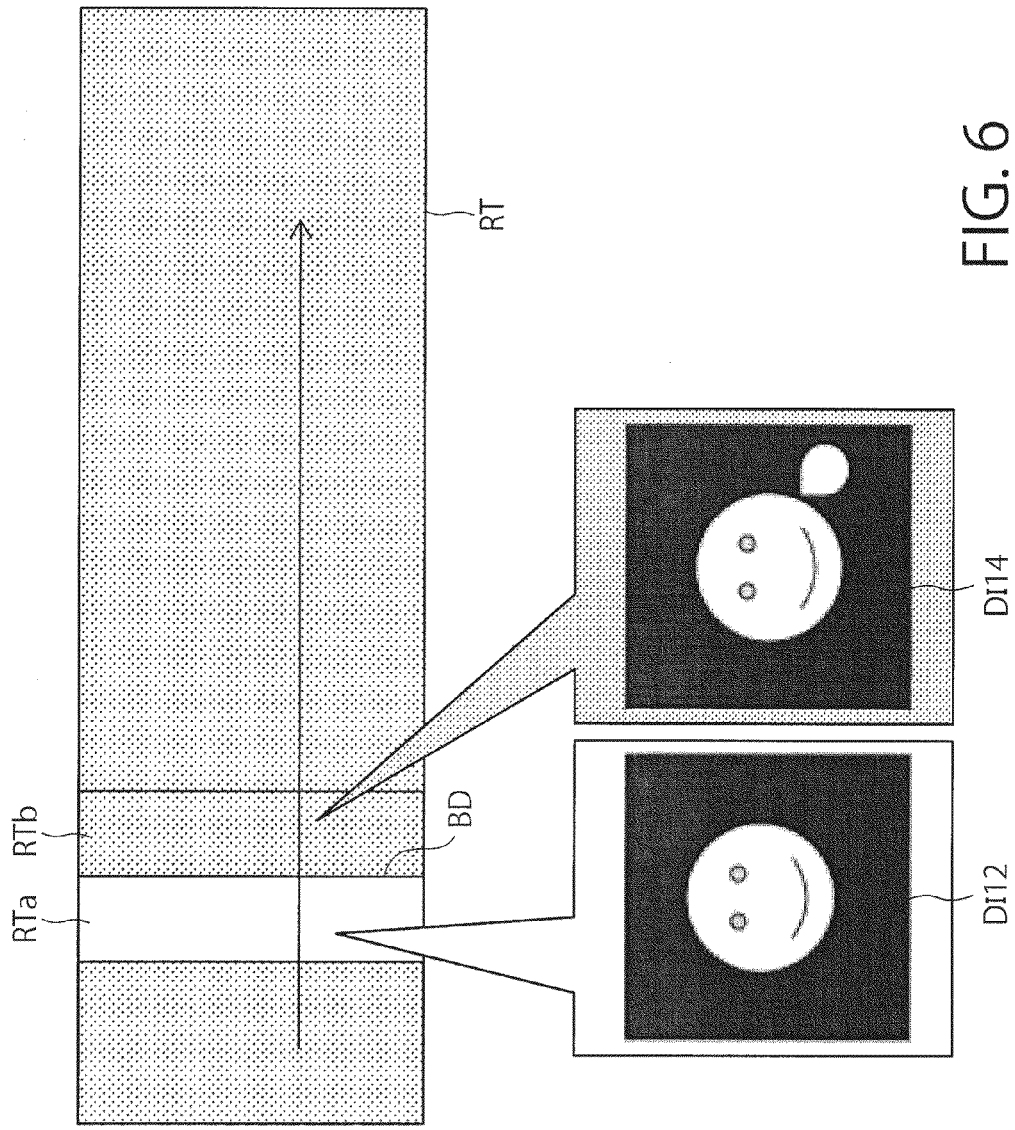
FIG. 6 is a diagram illustrating the technical meaning of extreme values calculated by the sample structure analyzing method according to Embodiment 2.

FIG. 6 is a diagram schematically showing how the extreme values of the luminance difference are found. A rectangular region RT in the upper part schematically represents data regarding the luminance difference between the diffraction images. In FIG. 6 the data are recorded from left to right. An arrow in the drawing represents the calculation to find the extreme values of the luminance difference. A boundary BD between data regions RTa and RTb corresponds to one extreme value. This boundary BD corresponds to, for example, a crystal grain boundary CI (12, 14) between the regions AR12 and AR14 in FIG. 4.

Thus, according to the present embodiment, the luminance difference between the diffraction images is differentiated to find extreme values, and the coordinates of the pixels that provide the obtained extreme values are connected. Therefore, a locus of a crystal grain boundary can be rapidly found by calculation processing.

When the locus of the crystal grain boundary identified by the process described above is used to scan the sample 10 with the electron beam in such a manner that the locus of the crystal grain boundary will be the center of each scan line, a transmission electron image of the crystal grain boundary can be acquired. This is possible if, for example, a locus of a crystal grain boundary is extracted from the memory MR4 by the control unit 52 of the transmission electron microscope shown in FIG. 2 and a control signal is generated and sent to the deflector 132 and the actuator 136.

The sample structure analyzing method according to at least one of the embodiments described above has the steps of comparing a plurality of diffraction images acquired from a beam which has passed through a sample, and judging the difference between the observation regions from the comparison result, or identifying the grain boundary of crystal constituting the sample. Consequently, it is possible to accurately distinguish crystal grain faces that would be difficult to distinguish by contrast comparison between images, and it is also possible to find a locus of a crystal grain boundary.

The transmission electron microscope according to at least one of the embodiments described above has analyzing unit for comparing a plurality of diffraction images acquired from a beam which has passed through a sample, and judging the difference between the observation regions from the comparison result, or identifying the grain boundary of crystal constituting the sample. Consequently, it is possible to accurately distinguish crystal grain faces which would be difficult to distinguish by contrast comparison between images, and it is also possible to find a locus of a crystal grain boundary.

(3) Program

A series of procedures in the sample structure analysis described above may be incorporated in a program, and read into and executed by a computer. This enables a series of procedures in the sample structure analysis according to Embodiments 1 and 2 to be carried out by use of a general-purpose computer connected to the main unit of the transmission electron microscope. A series of procedures of the sample structure analysis described above may be stored in a recording medium such as a flexible disk or a CD-ROM as a program to be executed by the computer connected to the main unit of the transmission electron microscope, and read into and executed by the computer.

The recording medium is not limited to a portable medium such as a magnetic disk or an optical disk, and may be a fixed recording medium such as a hard disk drive or a memory. The program incorporating the series of procedures of the sample structure analysis described above may be distributed via a communication line (including wireless communication) such as the Internet. Moreover, the program incorporating the series of procedures of the sample structure analysis described above may be distributed in an encrypted, modulated or compressed state via a wired line or a wireless line such as the Internet or in a manner stored in a recording medium.

The program according to at least one of the embodiments described above has the procedure for comparing a plurality of diffraction images acquired from a beam which has passed through a sample, and judging the difference between the observation regions from the comparison result, or identifying the grain boundary of crystal constituting the sample. Consequently, it is possible to accurately distinguish crystal grain boundaries and regions which would be difficult to distinguish by contrast comparison between images.

While certain embodiments have been described, these embodiments have been presented by way of example only, and are not intended to limit the scope of the inventions.

For example, the scanning transmission electron microscope (STEM) capable of scanning with the electron beam is shown in the embodiments described above, but the present invention is not limited thereto. For example, the sample analyzing method according to the embodiments described above can also be conducted by use of a transmission electron microscope (TEM) which includes a sample moving mechanism such as the actuator 136 shown in FIG. 2.

Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A sample structure analyzing method comprising:
   generating a beam and then applying the beam to a plurality of observation regions on a sample, and acquiring a plurality of diffraction images from the beam which has passed through the sample; and
   comparing the acquired diffraction images, and judging the difference between the observation regions from the comparison result, or identifying the grain boundary of crystal constituting the sample.

2. The method of claim 1,
   wherein the difference between the observation regions is judged by extracting feature amounts of each of the diffraction images, and comparing the feature amounts between the diffraction images by use of a predetermined threshold.

3. The method of claim 2,
   wherein extracting the feature amounts comprises extracting a pattern edge of each diffraction image, and
   comparing the feature amounts comprises performing pattern matching between the diffraction images to calculate a matching score, and comparing obtained matching score with the threshold.

4. The method of claim 3,
   wherein when the matching score is more than the threshold, judgment is made that the correlation between the diffraction images is high, and that the corresponding observation regions are regions of the same crystal, and
   wherein when the matching score is equal to or less than the threshold, judgment is made that the correlation between the diffraction images is low, and that the corresponding observation regions are regions of crystal different in at least one of material and crystal orientation.

5. The method of claim 2,
   wherein the threshold comprises
   a first threshold to judge whether materials are the same and whether crystal orientations are the same, and
   a second threshold to judge whether materials are different.

6. The method of claim 1,
   wherein the diffraction images are composed of pixels comprising luminance information, and
   identifying the crystal grain boundary comprises
   finding the difference of luminance value between the diffraction images, and differentiating obtained luminance difference to obtain extreme values, and obtaining a locus of the crystal grain boundary from the extreme values.

7. The method of claim 6, further comprising:
scanning the sample with the beam in such a manner that scanning area comprises the locus of the crystal grain boundary, and thereby acquiring a transmission electron image of the crystal grain boundary.

8. The method of claim 1, further comprising:
generating a beam and then applying the beam to a sample, and acquiring a transmission electron image from the beam which has passed through the sample,
wherein the observation regions are selected in accordance with obtained transmission electron image.

9. The method of claim 1,
wherein the diffraction images are acquired by scanning the sample with the beam.

10. The method of claim 1,
wherein the beam is applied for each pitch which corresponds to a size of crystal constituting the sample.

11. A transmission electron microscope comprising:
a beam applying unit configured to generate a beam and apply the beam to a sample;
a diffraction image acquiring unit configured to acquire a diffraction image from each of a plurality of observation regions of the sample from the beam which has passed through the sample; and
an analyzing unit configured to compare the acquired diffraction images, and judge difference between the observation regions from the comparison result, or identify the grain boundary of crystal constituting the sample.

12. The microscope of claim 11,
wherein the analyzing unit judges the difference between the observation regions by extracting feature amounts of each of the diffraction images, and by comparing the feature amounts between the diffraction images by use of a predetermined threshold.

13. The microscope of claim 11,
wherein the diffraction images are composed of pixels comprising luminance information, and
the analyzing unit identifies the crystal grain boundary by finding the difference of luminance value between the diffraction images, differentiating obtained luminance difference to find extreme values, and obtaining a locus of the crystal grain boundary from the extreme values.

14. The microscope of claim 11, further comprising:
a beam deflecting unit configured to deflect the beam to scan the sample.

15. The microscope of claim 11, further comprising:
a sample moving unit configured to move the sample to scan the sample with the beam.

16. A computer-readable non-transitory recording medium containing a program which causes a computer controlling a transmission electron microscope to execute a sample structure analysis, the sample structure analysis comprising:
generating a beam and then applying the beam to a plurality of observation regions on a sample, and acquiring a plurality of diffraction images from the beam which has passed through the sample; and
comparing the acquired diffraction images, and judging the difference between the observation regions from the comparison result, or identifying the grain boundary of crystal constituting the sample.

\* \* \* \* \*